United States Patent
Zhang et al.

(10) Patent No.: US 9,205,180 B2
(45) Date of Patent: Dec. 8, 2015

(54) METHOD AND DEVICE FOR LOADING MEDICAL APPLIANCE WITH MEDICAMENTS AND/OR POLYMERS

(75) Inventors: Jie Zhang, Shanghai (CN); Bo Yi, Shanghai (CN); Changsheng Wu, Shanghai (CN); Zhirong Tang, Shanghai (CN); Qiyi Luo, Shanghai (CN)

(73) Assignee: SHANGHAI MICROPORT MEDICAL (GROUP) CO., LTD., Pudong New Area, Shanghai (CN)

( * ) Notice: Subject to any disclaimer, the term of this patent is extended or adjusted under 35 U.S.C. 154(b) by 441 days.

(21) Appl. No.: 13/522,819

(22) PCT Filed: Jan. 19, 2011

(86) PCT No.: PCT/CN2011/000215
§ 371 (c)(1),
(2), (4) Date: Jul. 18, 2012

(87) PCT Pub. No.: WO2011/088755
PCT Pub. Date: Jul. 28, 2011

(65) Prior Publication Data
US 2012/0294499 A1    Nov. 22, 2012

(30) Foreign Application Priority Data
Jan. 19, 2010 (CN) .......................... 2010 1 0022937

(51) Int. Cl.
*A61L 33/00* (2006.01)
*A61L 31/06* (2006.01)
(Continued)

(52) U.S. Cl.
CPC .................. *A61L 31/06* (2013.01); *A61L 31/16* (2013.01); *A61F 2/91* (2013.01); *A61F 2250/0068* (2013.01); *A61L 2300/416* (2013.01)

(58) Field of Classification Search
CPC ....................................................... A61L 27/00
USPC ............... 427/2.24, 2.25, 2.28, 2.3, 261, 286, 427/287; 623/1.46
See application file for complete search history.

(56) References Cited

U.S. PATENT DOCUMENTS

| 6,395,326 B1 * | 5/2002 | Castro et al. .................. 427/2.24 |
| 7,785,653 B2 | 8/2010 | Shanley et al. |

(Continued)

FOREIGN PATENT DOCUMENTS

| CN | 1287872 | 12/2006 |
| CN | 1299836 | 2/2007 |

(Continued)

OTHER PUBLICATIONS

International Search Report for Application No. PCT/CN2011/000215 dated Apr. 28, 2011 (5 pages).

*Primary Examiner* — Dah-Wei D Yuan
*Assistant Examiner* — Andrew Bowman
(74) *Attorney, Agent, or Firm* — Michael Best & Friedrich LLP

(57) ABSTRACT

A method and a device for loading a medical appliance with a medicament and/or polymer includes capturing images of a plurality of grooves or holes of the medical appliance using an image capturing device; performing digital image processing on the image of each of the grooves or holes to obtain a pattern of each of the grooves or holes; calculating a central position of the pattern of each of the grooves or holes, and determining a loading position of each of the grooves or holes based on the central position; and adjusting a relative position between a loading device and the medical appliance to align an outlet of the loading device with the loading position of the medical appliance, and loading each of the grooves or holes with the medicament and/or polymer. The method and device can load the medical appliance with the medicament and/or polymer fast and efficiently.

12 Claims, 4 Drawing Sheets

(51) Int. Cl.
*A61L 31/16* (2006.01)
*A61F 2/91* (2013.01)

(56) References Cited

U.S. PATENT DOCUMENTS

2006/0222679 A1 10/2006 Shanley et al.
2006/0222755 A1 10/2006 Diaz et al.
2008/0077218 A1 3/2008 McMorrow et al.

FOREIGN PATENT DOCUMENTS

| WO | 2004012784 | 2/2004 |
| WO | 2004026182 | 4/2004 |
| WO | 2011012045 | 2/2011 |
| WO | 2011088755 | 7/2011 |

* cited by examiner

METHOD AND DEVICE FOR LOADING MEDICAL APPLIANCE WITH MEDICAMENTS AND/OR POLYMERS

CROSS-REFERENCE TO RELATED APPLICATIONS

This application is a national stage filing under 35 U.S.C. 371 of International Application No. PCT/CN2011/000215 filed Jan. 19, 2011, which claims foreign priority benefits to Chinese Patent Application No. 201010022937.0 filed Jan. 19, 2010. These applications are incorporated herein by reference in their entirety.

TECHNICAL FIELD

The present invention relates to the field of a medical instrument, and particularly to a method and a device for loading a medical appliance with a medicament and/or polymer.

BACKGROUND

A medicament eluting stent is a new technology for treating coronary heart diseases that is developed in recent years. A medicament eluting stent can be also called as a medicament releasing stent that carries a medicament via a polymer coated on a surface of the medicament eluting stent. When the stent is implanted into a lesion site within a blood vessel, the medicament releases controllably in a manner of eluting from the polymer coating into the cardiovascular wall tissue to exert the biological effect.

A single-sided coating manner is a newest manner of coating a medicament on a stent surface at present. Specifically, in the single-sided coating manner, a large amount of ever-indeformable small apertures capable of storing a medicament, which are called grooves or holes that may provide a medicament elution, are processed on the surface of a medicament eluting stent. The grooves or holes on the medicament elution stent are in a magnitude order of micron, so it is necessary to load a medicament and/or polymer with a dedicated method and device for loading.

In a process of carrying out the present application, the inventor found out that in the existing technology only one image of the storage grooves or holes can be obtained every time the medicament eluting stent performs the medicament and/or polymer loading, and the grooves or holes on the image are loaded after calculating a central position of the storage grooves or holes in the image. The aforesaid method for loading has the defects of a low loading speed and a low loading efficiency when performing loading.

SUMMARY OF INVENTION

In order to solve the aforesaid technical problem, the embodiment of the present application provides a method and device for loading a medical appliance with a medicament and/or polymer to load grooves or holes with the medicament and/or polymer fast and efficiently. The technical solution is as follows:

A method for loading a medial appliance with a medicament or polymer, wherein the medical appliance contains a plurality of grooves or holes for being loaded with the medicament and/or polymer, characterized in comprising:

capturing images of the grooves or holes of the medical appliance for multiple times using an image capturing device, each image containing a pattern of at least one entire the groove or hole;

performing digital image processing on the image of each of the grooves or holes to obtain the pattern of each of the grooves or holes;

calculating a central position of the pattern of each of the grooves or holes based on the pattern of each of the grooves or holes, and determining a loading position of each of the grooves or holes based on the central position; and adjusting a relative position between a loading device and the medical appliance to align an outlet of the loading device with the loading position of each of the grooves or holes, and loading each of the grooves or holes with the medicament and/or polymer.

Preferably, the image processing is embodied as:

image converting that converts the image of each of the grooves or holes into a set of pixel points;

image pre-processing that performs a filter processing on the set of pixel points to remove image noise; and image processing that processes the pre-processed image with a binary method to obtain the pattern of each of the grooves or holes.

Preferably, the processing with the binary method is embodied as:

assigning a value to each of the pixel points with the binary method based on a gray value of each of the pre-processed pixel points, designating a pixel point conforming with a preset value or value range as a target pixel point or a background pixel point, and connecting all the pixel points designated as the target pixel points or the background pixel points to obtain the pattern of each of the grooves or holes.

Preferably, the calculating the central position of the pattern of each of the grooves or holes and determining the loading position of each of the grooves or holes based on the central position is embodied as:

calculating a spatial coordinate of a central pixel point of the pattern of each of the grooves or holes based on a spatial coordinate of each of the pixel points of the pattern of each of the grooves or holes;

determining a spatial coordinate of a geometrical center of the image of each of the grooves or holes;

calculating a coordinate difference value in the x direction and/or in the y direction between the spatial coordinate of the central pixel point of the pattern of each of the grooves or holes and the spatial coordinate of the geometrical center of the image of each of the grooves or holes, and recording it as a first relative position; and recording the first relative position corresponding to each of the grooves or holes as a first array.

Preferably, the determining the spatial coordinate of the geometrical center of the image of each of the grooves or holes is embodied as:

obtaining spatial coordinates of four apexes of the image of each of the grooves or holes; and calculating the spatial coordinate of the geometrical center of the image of each of the grooves or holes based on the spatial coordinates of the four apexes.

Preferably, the calculating the central position of the pattern of each of the grooves or holes, and determining the loading position of each of the grooves or holes based on the central position is embodied as:

calculating a pixel coordinate of the central pixel point of the pattern of each of the grooves or holes based on a pixel coordinate of each of the pixel points in the pattern of each of the grooves or holes;

determining a pixel coordinate of the pixel point of the geometrical center of the image of each of the grooves or holes;

calculating a coordinate difference value between the pixel coordinate of the central pixel point of the pattern of each of the grooves or holes and the pixel coordinate of the pixel point of the geometrical center of the image of each of the grooves or holes, converting the coordinate difference value between the two pixels points into a spatial coordinate difference value, and recording it as a first relative position; and recording the first relative position corresponding to each of the grooves or holes as a first array.

Preferably, the determining the pixel coordinate of the pixel point of the geometrical center of the image of each of the grooves or holes is embodied as:

obtaining pixel coordinates of four apexes of the image of each of the grooves or holes; and calculating the pixel coordinate of the geometrical center of the image of each of the grooves or holes based on the pixel coordinates of the four apexes.

Preferably, the calculating the pixel coordinate of the geometrical center of the image of each of the grooves or holes is embodied as:

obtaining a medium value of the pixel point respectively in an x direction and/or in a y direction based on a resolution of the image of each of the grooves or holes, the medium value being the pixel coordinate of the geometrical center of the image of each of the grooves or holes.

Preferably, the adjusting the relative position between the loading device and the medical appliance to align the outlet of the loading device with the loading position of the medical appliance is embodied as:

determining a relative position of the loading device to the image capturing device, and recording it as a second relative position; and adjusting a relative position between the loading device and the medical appliance based on the first relative position and the second relative position to cause the outlet of the loading device and the central position of the pattern of each of the grooves or holes to be in the same longitudinal axis.

Preferably, the determining the relative position of the loading device to the image capturing device, and recording it as the second relative position is embodied as:

obtaining a spatial coordinate of the center of the image capturing device;

obtaining a spatial coordinate of the outlet of the loading device;

calculating a coordinate difference value in a x direction and/or in a y direction between the spatial coordinate of the center of the image capturing device and the spatial coordinate of the outlet of the loading device, and recording it as a second relative position.

Preferably, the adjusting the relative position between the loading device and the medical appliance based on the first relative position and the second relative position is embodied as:

moving the medical appliance in the x direction and/or in the y direction based on the first relative position and the second relative position to cause outlet of the loading device and the central position of the pattern of each of the grooves or holes to be in the same longitudinal axis.

Preferably, the adjusting the relative position between the loading device and the medical appliance based on the first relative position and the second relative position is embodied as:

moving the medical appliance in the x direction and/or in the y direction based on the first relative position to cause the central position of the pattern of each of the grooves or holes and the geometrical center of the image to be in the same longitudinal axis; and moving the loading device in the x direction and/or in the y direction based on the second relative position to cause the outlet of the loading device and the central position of the pattern of each of the grooves or holes to be in the same longitudinal axis.

Preferably, the adjusting the relative position between the loading device and the medical appliance to align the outlet of the loading device with the loading position of the medical appliance is embodied as:

moving the image capturing device in the x direction and/or in the y direction based on the first relative position in the first array to cause the central position of the pattern of each of the grooves or holes and the geometrical center of the image of each of the grooves or holes to be in the same longitudinal axis;

determining a relative position of the loading device to the image capturing device, recording it as a second relative position, recording the second relative position corresponding to each of the grooves or holes as a second array; and adjusting a relative position between the loading device and the medical appliance based on the second relative position in the second array to cause the outlet of the loading device and the central position of the pattern of each of the grooves or holes to be in the same longitudinal axis.

Preferably, the determining the relative position of the loading device to the image capturing device, recording it as the second relative position is embodied as:

obtaining a spatial coordinate of a center of the image capturing device;

obtaining a spatial coordinate of an outlet of the loading device;

calculating a coordinate different value in the x direction and/or in the y direction between the spatial coordinate of the center of the image capturing device and the spatial coordinate of the outlet of the loading device, and recording it as a second relative position; and recording the second relative position corresponding to each of the grooves or holes as a second array.

Preferably, adjusting the relative position between the loading device and the medical appliance based on the second relative position is embodied as:

moving the medical appliance in the x direction and/or in the y direction based on the second relative position in the second array to cause the outlet of loading device and the central position of the pattern of each of the grooves or holes to be in the same longitudinal axis.

Preferably, the adjusting the relative position between the loading device and the medical appliance based on the second relative position is embodied as:

moving the loading device in the x direction and/or in the y direction based on the second relative position in the second array to cause the outlet of loading device and the central position of the pattern of each of the grooves or holes to be in the same longitudinal axis.

Preferably, the loading each of the grooves or holes with the medicament or polymer is embodied as:

after causing the outlet of loading device and the central position of the pattern of each of the grooves or holes to be in the same longitudinal axis, opening the outlet of the loading device to load the grooves or holes with the medicament and/or polymer; and loading each of the grooves or holes with the medicament and/or polymer.

Preferably, the loading each of the grooves or holes with the medicament and/or polymer is repeated for multiple times based on a desired dose of the medicament and/or polymer.

Preferably, the method further comprises adjusting the position between the medical appliance and the image capturing device to cause other grooves or holes of the medical appliance to be located at an image capture position of the image capturing device.

Preferably, the width of the grooves or holes is within 0.5-200 microns.

Preferably, the width of the grooves or holes is within 20-80 microns.

Preferably, the medical appliance is a human body endoluminal stent.

Preferably, the human body endoluminalendoluminal stent is a blood vessel stent.

Preferably, the medicament is selected from a chemical medicament and/or a bioactive substance.

Preferably, the chemical medicament is selected from an immunosuppressant and/or an anticancer medicament.

Preferably, the immunosuppressant is selected from rapamycin and derivatives thereof, and that the anticancer medicament is selected from paclitaxel and derivatives thereof.

Preferably, the bioactive substance includes protein, polypeptide, DNA, RNA and/or microRNA.

Preferably, the polymer is a biodegradable polymer.

Preferably, the biodegradable polymer is one or more selected from homopolymers and copolymers of $C_2$-$C_6$ acyclic hydroxycarboxylic acid composed of C, H, and O.

Preferably, the biodegradable polymer is:

(1) one or more of homopolymers of D-lactic acid, L-lactic acid, glycolic acid or ε-caprolactone; and/or (2) one or more of copolymers formed by more than any two from D-lactic acid, L-lactic acid, glycolic acid and ε-caprolactone as monomers.

Preferably, the biodegradable polymer is one or more selected from poly D, L-lactide, poly D-lactide, poly L-lactide, polyglycolide, poly(glycolide-lactide) and poly ε-caprolactone.

A device for loading a medial appliance with a medicament and/or polymer, the medical appliance containing a plurality of grooves or holes, characterized in comprising:

a platform for placing the medical appliance;

an image capturing device disposed above the platform for capturing images of the grooves or holes of the medical appliance;

an image processing unit connected with the image capturing device for performing digital image processing on the images of the grooves or holes captured by the image capturing device;

a position calculating unit connected with the image processing unit for calculating a desired relative position based on a result processed by the image processing unit;

a memory unit connected with the position calculating unit for recording a relative position calculated by the position calculating unit;

a first position adjustment device connected with the memory unit and with the platform for moving the platform based on the relative position in the memory unit to adjust a relative position relation between the medical appliance and the image capturing device and/or the loading device; and a loading device disposed above the platform for loading the grooves or holes of the medical appliance with the medicament and/or polymer.

Preferably, the device further comprises a position calibration device connected with the memory unit for calibrating a spatial position relation between a central position of the image capturing device and an outlet of the loading device.

Preferably, the platform comprises a rotation platform and a stent shaft, the stent shaft fixed in and penetrated through the middle of the rotation platform, and the medical appliance disposed on the stent shaft.

Preferably, the image capturing device is a camera or video camera.

Preferably, the image capturing device is an industrial camera or video camera.

Preferably, the image processing unit comprises:

an image converting sub-unit for converting the image of the groove or hole into a set of pixel points;

an image pre-processing sub-unit for performing a filter processing on the set of pixel points to remove image noise; and an image processing sub-unit for processing the pre-processed image with a binary method to obtain the pattern of each of the grooves or holes.

Preferably, the image processing sub-unit assigns a value to each of the pixel points with the binary method based on a gray value of each of the pre-processed pixel points, designates a pixel point conforming with a preset value or a value range as a target pixel point or a background pixel point, and connects all the pixel points designated as the target pixel points or the background pixel points to obtain the patterns of the grooves or holes.

Preferably, the device further comprises:

a second position adjustment device connected with the memory unit and with the image capturing device for driving the image capturing device to move on a horizontal coordinate plane based on the relative position in the memory unit.

Preferably, the device further comprises:

a third position adjustment device connected with the memory unit and with the loading device for driving the loading device to move in a horizontal plane based on the relative position in the memory unit.

Preferably, an axis of the image capturing device and an axis of the loading device are disposed in the same vertical plane.

Preferably, the width of the grooves or holes of the medical appliance is within 0.5-200 microns.

Preferably, the width of the grooves or holes of the medical appliance is within 20-80 microns.

Preferably, the medical appliance is a human body endoluminal stent.

Preferably, the human body endoluminal stent is a blood vessel stent.

Preferably, the medicament includes a chemical medicament and/or a bioactive substance.

Preferably, the chemical medicament is selected from an immunosuppressant and/or an anticancer medicament.

Preferably, the immunosuppressant is selected from rapamycin and derivatives thereof, and that the anticancer medicament is selected from paclitaxel and derivatives thereof.

Preferably, the bioactive substance is selected from protein, polypeptide, DNA, RNA and/or microRNA.

Preferably, the polymer is a biodegradable polymer.

Preferably, the biodegradable polymer is one or more selected from homopolymers and copolymers of $C_2$-$C_6$ acyclic hydroxycarboxylic acid composed of C, H, and O.

Preferably, the biodegradable polymer is:

(1) one or more of homopolymers of D-lactic acid, L-lactic acid, glycolic acid or ε-caprolactone; and/or (2) one or more of copolymers formed by more than any two from D-lactic acid, L-lactic acid, glycolic acid and ε-caprolactone as monomers.

Preferably, the biodegradable polymer is one or more selected from poly D,L-lactide, poly D-lactide, poly L-lactide, polyglycolide, poly(glycolide-lactide) and poly ε-caprolactone.

In the embodiments of the present application, the images of the grooves or holes of the medical appliance containing a plurality of grooves or holes are captured for multiple times, the image of each of the grooves or holes is processed, and then each of the grooves or holes is loaded concentratively, reducing the displacement movement route during the process of loading, shortening the loading time, and improving the loading speed and efficiency.

Besides, the embodiments of the present application search a groove core or a hole core using a machine visual theory, precisely locate each of the grooves or holes of the medical appliance, provide a precise coordinate for loading a medicament and/or polymer, and ensure the loading accuracy while loading rapidly.

Furthermore, the embodiments of the present application employ the intermittent loading manner, reduce the time waiting for evaporation of the medicament and/or polymer, not only shorten the loading time, but also make the loaded medicament and/or polymer more even, and improve the quality of loading the medicament and/or polymer.

DESCRIPTION OF DRAWINGS

In order to explain the embodiments of the present application or the technical solutions in the existing technologies more clearly, the drawings to be referred to in depictions of the embodiments and the existing technologies are briefly introduced below. Obviously, the drawings depicted below are only some embodiments disclosed in the present application. An ordinary skilled person in the art can obtain other drawings without inventive efforts.

DETAILED DESCRIPTION OF PREFERRED EMBODIMENTS

In order to enable those skilled in the art to better understand the technical solution of the present application, the technical solutions in the embodiments of the present application will be depicted clearly and completely with reference to the drawings in the embodiments of the present application. Obviously, the depicted embodiments are only a part of the embodiments of the present application rather than all the embodiments. Based on the embodiments of the present application, all the other embodiments that can be obtained by an ordinary skilled in the art without inventive efforts shall fall into the scope claimed in the present application.

FIG. 1 is the blood vessel stent having grooves or holes used in the present application and a drawing of a partial enlargement thereof.

Figure 1A:
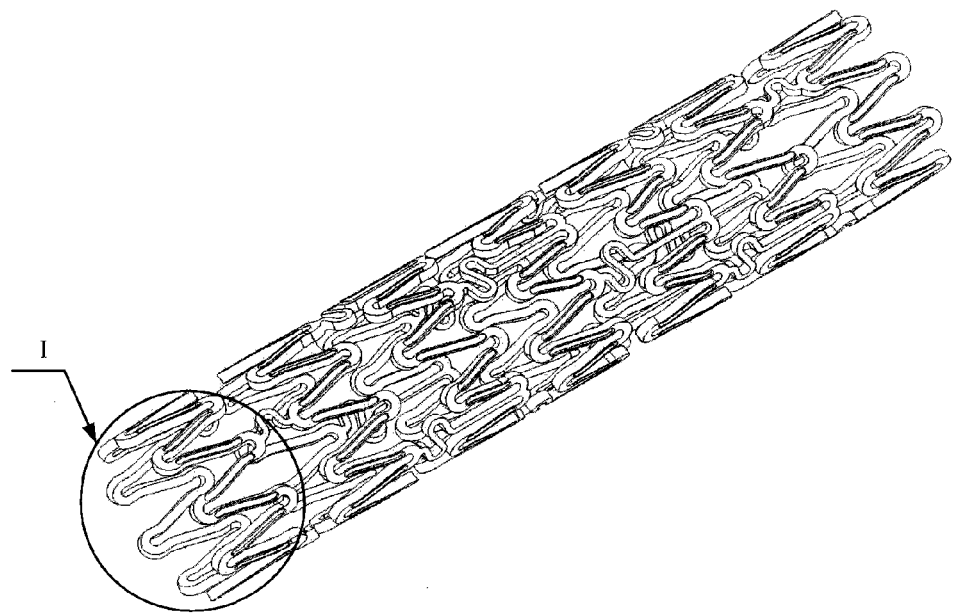
FIG. 1 is a structural drawing of the blood vessel stent having grooves or holes used in the present application and a drawing of a partial enlargement thereof.
Figure 1B:
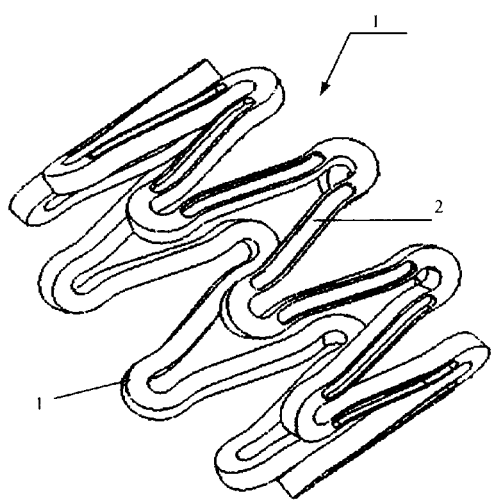

FIG. 1(a) shows a blood vessel stent that is formed by cutting a metal circular tube roughcast with a laser cutter, wherein on an outer surface of the stent grooves or holes having a depth of 30 microns, a width of 50 microns, and a length of 500 microns are etched, and on each stent there are a plurality of rings. I shows the drawing of the partial enlargement of one ring. As shown in FIG. 1(b), 1 is a strut, and 2 is a groove or hole. There are a plurality of struts on every ring, and there is one groove or hole on each strut.

A medicament and/or polymer is loaded within the groove or hole, and the loaded medicament may be a chemical medicament and/or bioactive substance. The chemical medicament includes an immunosuppressant selected from rapamycin and derivatives thereof and/or an anticancer medicament selected from paclitaxel and derivatives thereof. The bioactive substance includes protein, polypeptide, DNA, RNA and/or microRNA.

The loaded polymer may be a biodegradable polymer. The biodegradable polymer is one or more selected from homopolymers and copolymers of $C_2$-$C_6$ acyclic hydroxycarboxylic acid composed of C, H, and O.

Alternatively, the above-mentioned biodegradable polymer is:

(1) one or more of homopolymers of D-lactic acid, L-lactic acid, glycolic acid or ε-caprolactone; and/or (2) one or more of copolymers formed by more than any two from D-lactic acid, L-lactic acid, glycolic acid and ε-caprolactone as monomers.

Alternatively, the above-mentioned biodegradable polymer is one or more selected from poly D,L-lactide, poly D-lactide, poly L-lactide, polyglycolide, poly(glycolide-lactide) and poly ε-caprolactone.

Embodiment 1 of the Method

Figure 2:
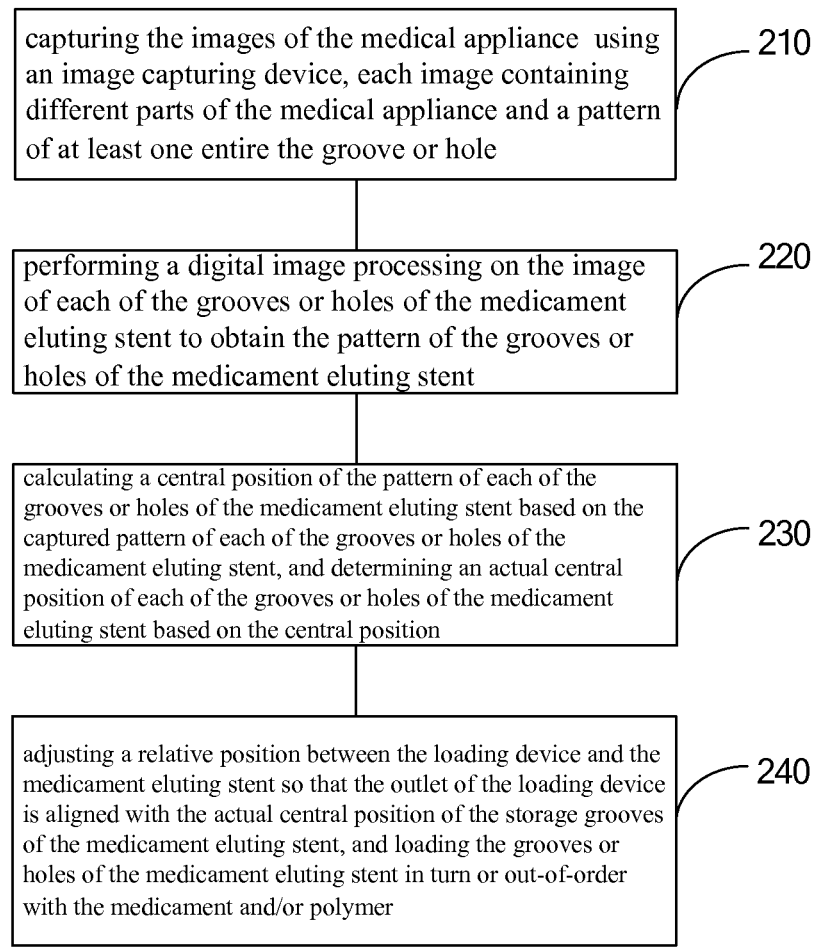
FIG. 2 is a flow chart of one method for loading a medical appliance with a medicament and/or polymer provided by the embodiments of the present invention.

In the present embodiment, the medical appliance is specifically a blood vessel stent. The embodiment of the present application provides a method for loading a medical appliance with a medicament or polymer, comprising the following steps as shown in FIG. 2:

In step 210, images of the blood vessel stent are captured for multiple times using an image capturing device, each image containing a pattern of at least one entire the groove or hole.

When the blood vessel stent is relatively long, the grooves or holes on one or more rings of the blood vessel stent may be photographed for multiple times at one time. When the blood vessel stent is relatively short, the grooves or holes on all the rings of the blood vessel stent can be photographed at one time. The captured images of the grooves or holes can be recorded as one set of images, of which each image contains one groove or hole in one strut. Assume that there are m images in the set of images, then there are m grooves or holes all together.

In step 220, digital image processing is performed on the image of each of the grooves or holes of the blood vessel stent to obtain the pattern of each of the grooves or holes.

Firstly, the image of each of the grooves or holes is converted into a set of pixel points. After the image is converted into the set of pixel points, the set of pixel points is filtering processed to remove disturbing noise of the image.

Secondly, image processing is performed on the pre-processed image. Mainly, the pre-processed image is processed with a binary method, in which values are assigned to the pixel points based on a gray value of each of the pixel points, a pixel point conforming with a preset value or value range is designated as a target pixel point or a background pixel point, and all the pixel points designated as the target pixel points or the background pixel points are connected to form a target pixel body, i.e., the pattern of the groove or hole of the blood vessel stent, to obtain the images of m grooves or holes.

In step 230, a central position of the pattern of each of the grooves or holes of the blood vessel stent is calculated based on the captured pattern of each of the grooves or holes of the blood vessel stent, and a loading position of each of the grooves or holes of the blood vessel stent is determined based on the central position.

Firstly, a spatial coordinate of a central pixel point of the pattern of each of the grooves or holes of the blood vessel stent is calculated.

Figure 3:
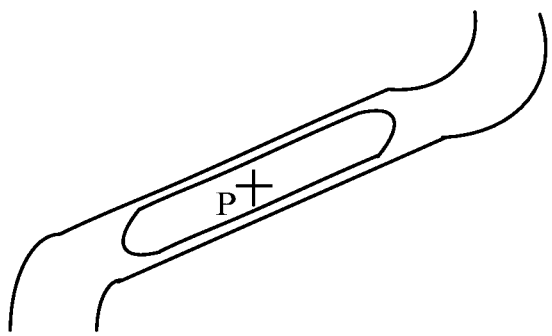
FIG. 3 is a flow chart of another method for loading a medical appliance with a medicament and/or polymer provided by the embodiments of the present invention.

Based on the pattern of the m grooves or holes obtained in step 220, as shown in FIG. 3, the central pixel point P is the central potion of the pattern of each of the grooves or holes. The pixel coordinate of the central pixel point P is obtained, and then is converted to obtain the spatial coordinate (A, B) of the central pixel point P.

Secondly, a spatial coordinate of a geometrical center of the image of each of the grooves or holes of the blood vessel stent is determined.

Spatial coordinates of four apexes of the image are obtained based on the image of the groove or hole, the spatial coordinate (A', B') of the geometrical center of the image of each of the grooves or holes of the blood vessel stent, i.e., the central position of the image capturing device, is calculated based on the spatial coordinates of the four apexes.

Finally, a difference value between the spatial coordinate (A, B) of the central pixel point and the spatial coordinate (A', B') of the geometrical center is calculated, and represented in a form of a coordinate (A-A', B-B'). That is, it is necessary to adjust the distances A-A' and B-B' respectively in the x direction and/or in the y direction so that the spatial coordinate (A, B) of the central position of the pattern of the groove or hole and the spatial coordinate (A', B') of the geometrical center of the image are in the same longitudinal axis.

The m grooves or holes are subject to the aforesaid calculation. The difference values (A-A', B-B') between the coordinates corresponding to m grooves or holes are recorded as a first array.

In step 240, a relative position of the loading device to the blood vessel stent is adjusted so that the outlet of the loading device is aligned with the loading position of the storage grooves or holes of the blood vessel stent for loading the grooves or holes of the blood vessel stent with the medicament and/or polymer. The step includes the following steps:

In step 241, a relative position of the loading device to the image capturing device is determined and recoded as a second relative position.

The spatial coordinate of the center of the image capturing device and the spatial coordinate of the outlet of the loading device are obtained. A coordinate difference value between the spatial coordinate of the center of the image capturing device and the spatial coordinate of the outlet of the loading device in the x direction and/or in the y direction is calculated. If the coordinate difference value between the aforesaid two spatial coordinates in the x direction and/or in the y direction is set as (M, N), then (M, N) is recorded as a second relative position.

If the image capturing device and the loading device are fixed, the second relative position can be calculated in advance. If either of the aforesaid two devices exist relative displacement, it is necessary to calculate the second relative position in step 241.

In step 242, the blood vessel stent is moved based on the first relative position in the first array taking the central position of each image capturing device as the reference so that the central position of the pattern of each of the grooves or holes and the geometrical center of the image are in the same longitudinal axis.

A first element is selected from the array, the blood vessel stent is adjusted by moving in the x direction by A-A' and moving in the y direction by B-B' based on the recorded value of the first relative position (A-A', B-B') and taking the spatial coordinate (A', B') of the central position of the image as the reference so that the central position of the pattern of each of the grooves or holes and the center of the image capturing device are in the same longitudinal axis. That is, the loading position of the groove or hole superposes the center of the image capturing device in the vertical direction, and the loading position of the groove or hole is found.

In step 243, the blood vessel stent is moved taking the outlet of the loading device as the reference and based on the second relative position so that the loading position of each of the grooves or holes and the outlet of the loading device are in the same longitudinal axis.

The blood vessel stent is moved in the x direction and/or in the y direction respectively by M and N so that the loading position of the grooves or holes of the blood vessel stent and the outlet of the loading device are in the same longitudinal axis. The outlet of the loading device is opened so that the medicament and/or polymer pre-loaded into the device is dispensed via the outlet thereof into the groove or hole 2 of the blood vessel stent. The same operation is repeated to each of the grooves or holes to load it with the medicament and/or polymer.

The aforesaid step 242 and step 243 are moving the blood vessel stent respectively based on the first relative position and based on the second relative position, so the aforesaid two steps can be combined into one step.

Figure 4:
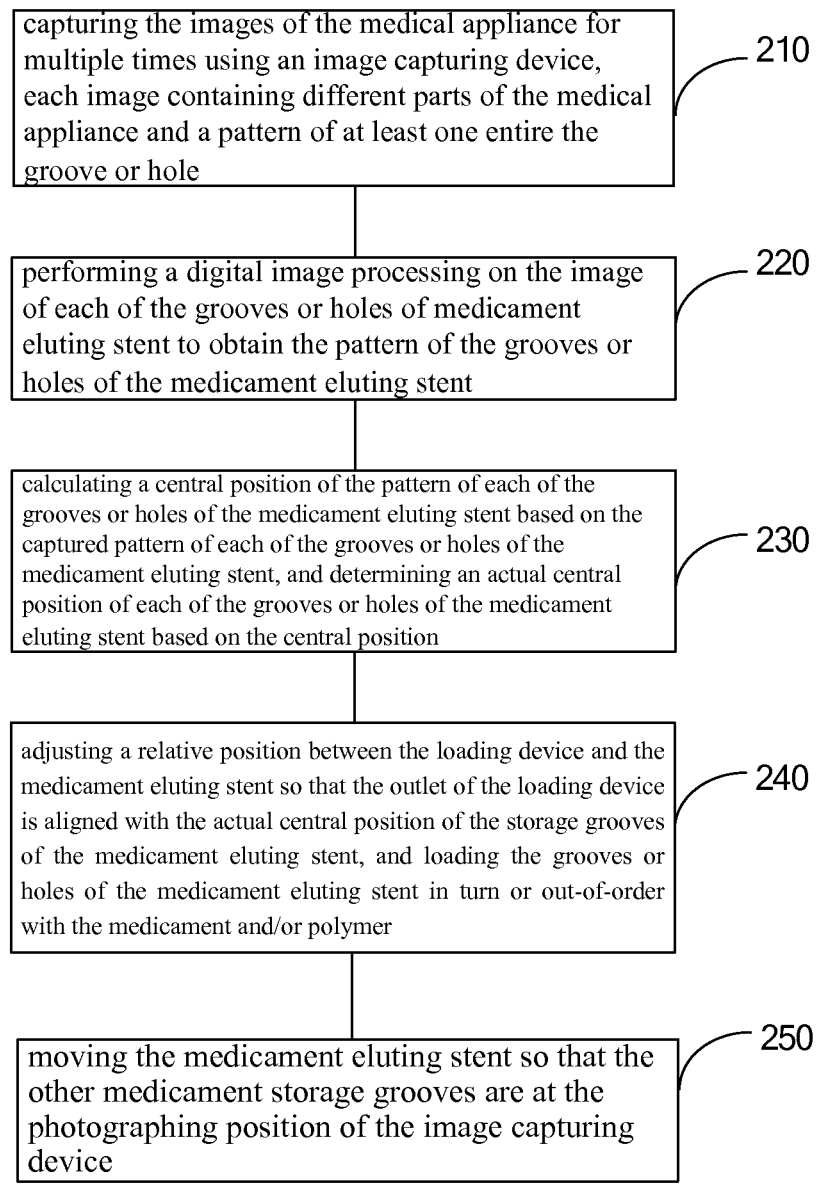
FIG. 4 is the image of the grooves or holes captured by the image capturing device according to the embodiments of the present application.

As shown in FIG. 4, after the completion of loading in step 240, step 250 may be further included, in which the relative position of the blood vessel stent to the image capturing device is adjusted so that the other medicament grooves of the blood vessel stent are at the photographing position of the image capturing device.

Steps 210 to 240 can realize loading a plurality of medicament grooves of the blood vessel stent. Where it is necessary to load all the grooves of the entire blood vessel stent, after completion of one loading, firstly the blood vessel stent is moved back within a photographing range of the image capturing device, secondly the blood vessel stent is rotated by a certain angle and/or translated by a certain distance so that other grooves or holes of the blood vessel stent move to the photographing position of the image capturing device. Thus, after the completion of loading a plurality of grooves or holes at one time, it is feasible to circularly load the other grooves or holes of the blood vessel stent, thereby completing loading the entire blood vessel stent.

It is known to those skilled in the art that the medical appliance in practical use may also be a biliary stent, an esophageal stent, a ureteral stent, or other human body endoluminal stents. Although the medical appliance in the present embodiment is a blood vessel stent, it shall not constitute a restriction on the present application.

Besides, depending on the desired dose of the medicament and/or polymer to be loaded, step 240 may be repeated for multiple times to avoid an excessive loading amount at one time from influencing the adhering effect of the medicament and/or polymer. Loading for multiple times can leave time for the medicament and/or polymer evaporating so that the loading is more even and the quality of loading the medicament and/or polymer is improved.

Embodiment 2 of the Method

In Embodiment 1 of the present invention, in step 230, the loading position of each of the grooves or holes of the blood vessel stent can be determined based on the pixel coordinate, which is specifically realized by the following steps:

Firstly, the pixel coordinate of the central pixel point of the pattern of each of the grooves or holes of the blood vessel stent is calculated.

According to the images of the m grooves or holes obtained in step 220, as shown in FIG. 3, the central pixel point P is the central potion of the pattern of each of the grooves or holes. The pixel coordinate value (a, b) of the central pixel point P is obtained.

Secondly, the pixel coordinate of the geometrical center of the image of each of the grooves or holes of the blood vessel stent is determined.

Pixel coordinates of four apexes of the image are obtained based on the photographed image of the groove or hole. The medium value of the pixel point in the x direction and/or in the y direction is obtained respectively based on the pixel coordinates of the four apexes and the resolution of each of the grooves or holes. The medium value is the pixel coordinate (a', b') of the geometrical center of the image of each of the grooves or holes of the blood vessel stent, and is also the center of the image capturing device.

Finally, the difference value between the pixel coordinate (a, b) of the central pixel point and the pixel coordinate (a', b') of the geometrical center. Likewise, the difference value is represented in the form of a coordinate (a-a', b-b'). That is, it is necessary to adjust the distances a-a' and b-b' respectively in the x direction and/or in the y direction so that the pixel coordinate (a, b) of the central position of the pattern of the groove or hole superposes the pixel coordinate (a', b') of the geometrical center of the image. That is, the central position of the pattern of the groove or hole superposes the center of the image capturing device, and the loading position of the groove or hole is found.

Embodiment 3 of the Method

In Embodiment 1 and/or Embodiment 2 of the present invention, in step 241, the image capturing device may be moved taking the central position of the pattern of each of the grooves or holes as the reference, and the step is as follows:

In step 242, the image capturing device is moved according to the first relative position in the first array taking the central position of each of the grooves or holes as the reference so that the central position of the pattern of each of the grooves or holes and the geometrical center of the image are in the same longitudinal axis.

A first element is selected from the array, the blood vessel stent is adjusted by moving in the x direction and/or in the y direction based on the recorded value of the first relative position and taking the spatial coordinate of the central position of each of the grooves or holes as the reference so that the center of the image capturing device and the central position of the pattern of each of the grooves or holes are in the same longitudinal axis. That is, the loading position of the groove or hole superposes the center of the image capturing device in the vertical direction, and the loading position of the groove or hole is found.

Embodiment 4 of the Method

In Embodiment 1, Embodiment 2, and/or Embodiment 3 of the present invention, in step 243, the loading device may also be moved taking the central position of the pattern of each of the grooves or holes as the reference, the step is as follows:

In step 243, the loading device is moved taking the central position of each of the grooves or holes as the reference and based on the second relative position so that the loading position of each of the grooves or holes and the outlet of the loading device are in the same longitudinal axis.

The loading device is moved in the x direction and/or in the y direction respectively by -M and -N so that the outlet of the loading device and the loading position of the grooves or holes of the blood vessel stent are in the same longitudinal axis. The outlet of the loading device is opened so that the medicament and/or polymer pre-loaded into the device is dispensed via the outlet thereof into the groove or hole 2 of the blood vessel stent. The same operation is repeated to each of the grooves or holes to load it with the medicament and/or polymer.

Corresponding to the above embodiments of the method, the present application further provides a device for loading a medical appliance with a medicament and/or polymer.

Embodiment 1 of the Device

Figure 5:
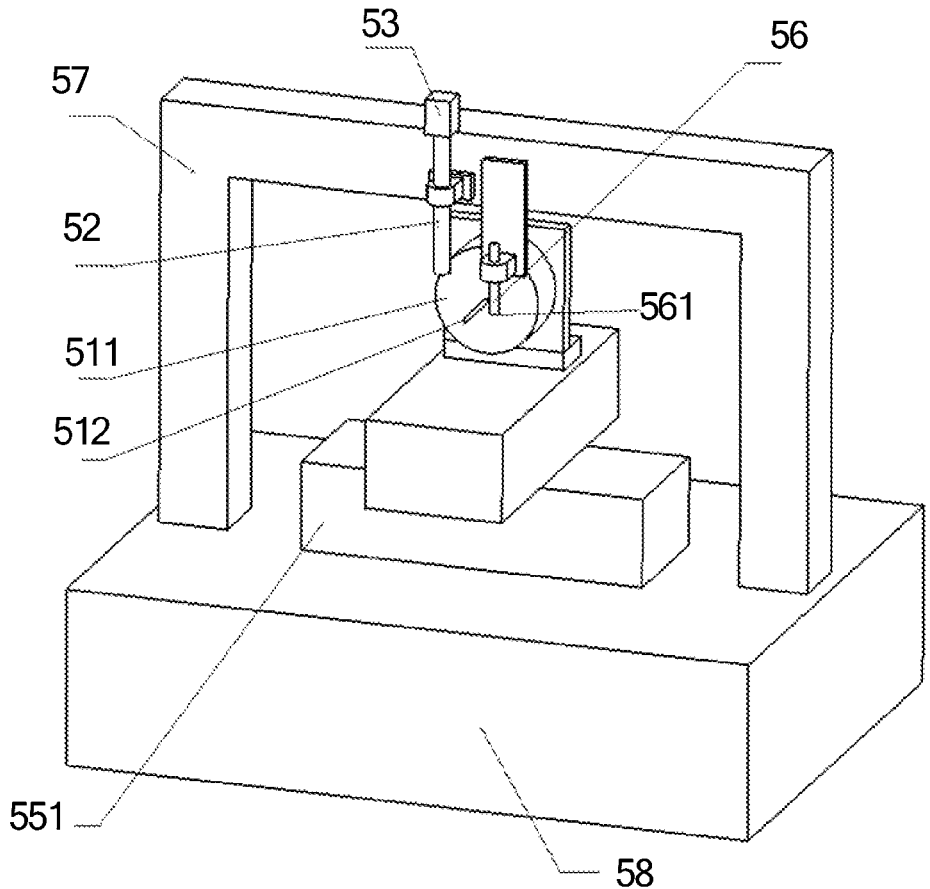
FIG. 5 is a schematic diagram of the structure of a device for loading a medical appliance with a medicament and/or polymer.

As shown in FIG. 5, the device comprises a platform, an image capturing device 52, an image processing unit 53 (not shown in the drawings), a position calculating unit 54 (not shown in the drawings), a first position adjustment device (not shown in the drawings), a memory unit (not shown in the drawings), a loading device 56, a gantry 57, and a base 58.

The platform comprises a rotation platform 511 and a stent shaft 512. The stent shaft 512 is through the middle of the rotation platform 511 and perpendicular to it, and fixed to the rotation platform 511. The rotation platform 511 may be of a circle or of another geometrical shape, and can rotate freely in a vertical plane.

The gantry 57 and the base 58 serve the purpose of fixing and supporting. The gantry 57 is disposed on the base 58, and is perpendicular to the base 58.

The image capturing device 52 is fixed on a beam of the gantry 57 and perpendicular to the beam of the gantry 57. The image processing unit 53 is connected to the image capturing device 52. The image capturing device 52 uses an industrial camera or video camera in practical use. When photographing a blood vessel stent, it is necessary to illuminate the blood vessel stent for making the photographed image clear. The present embodiment of the application employs two 12V brightness-adjustable power sources respectively for controlling a point light source and an annular light source for providing a required illumination.

The image processing unit 53 receives and processes the image photographed by the image capturing device 52 and sends the processed image data to the position calculating unit 54.

Figure 6:
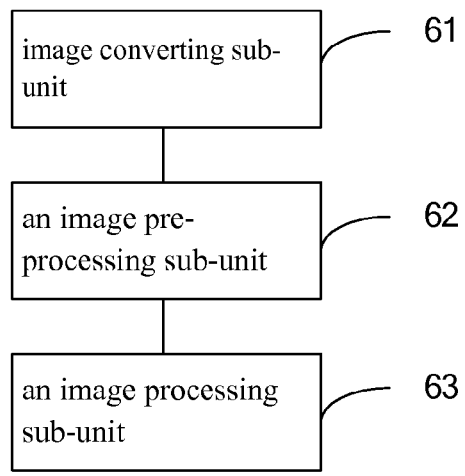
FIG. 6 is a schematic diagram of the structure of the image processing unit according to the embodiments of the present application.

As shown in FIG. 6, the image processing unit 53 comprises:

an image converting sub-unit 61 for converting the image of each of the grooves or holes captured by the image capturing device 52 into a set of pixel points;

an image pre-processing sub-unit 62 for performing a filter processing on the set of pixel points to remove image noise;

an image processing sub-unit 63 for processing the pre-processed image with a binary method to obtain the pattern of each of the grooves or holes;

a position calculating unit 54 for calculating based on the image data to obtain relative position data and sending the relative position data to the a memory unit; and a memory unit for storing the relative position data calculated by the position calculating unit 54, sending the recorded relative position data to a position adjustment device or to an externally visible part for an operator to proceed with a next operation.

The first position adjustment device comprises a control chip (not shown in the drawings) and a mobile device 551. The control chip receives relative position data in the memory unit to generate control instructions so as to control the mobile device 551 to move respectively in the x direction and/or in the y direction. The mobile device 551 is disposed in the gantry, and below the image capturing device 52. The platform is fixed on the mobile device 551, and the mobile device 551 moves in the x direction and/or in the y direction and can drive the platform to make a corresponding movement.

The loading device 56 is also fixed on a beam of the gantry 57, and also perpendicular to the beam of the gantry 57. The loading device 56 is pre-loaded with a desired medicament and/or polymer. The outlet of the loading device is 561.

In the embodiment of the present invention, in the process of loading, the first position adjustment device controls the mobile device 551 to move based on relative position data of the unit so as to drive the blood vessel stent on the platform to move. Firstly, the blood vessel stent is moved so that the central position of the groove or hole of the blood vessel stent and the central position of the image capturing device 52 are in the same longitudinal axis. Secondly, the blood vessel stent is moved again so that the central position of the groove or hole of the blood vessel stent and the outlet 561 of the loading device are in the same longitudinal axis. Finally, the outlet of the loading device is opened to perform the loading. During the aforesaid process of loading, it is only necessary to move the blood vessel stent so as to fulfill the loading, and the positions of the image capturing device 52 and the loading device 56 are constant.

During the process of loading, the first position adjustment device can control the mobile device 551 to move directly based on the first relative position data of the first relative position and the second relative position of the unit to move the blood vessel stent so that the central position of the groove or hole of the blood vessel stent and the outlet 561 of the loading device are in the same longitudinal axis. Then the outlet of the loading device is opened to perform the loading.

Embodiment 2 of the Device

In the embodiment of the present invention, the device further comprises:

a position calibration device for calibrating a spatial position relation between a central position of the image capturing device and an outlet of the loading device; and a second position adjustment device connected with the memory unit and with the image capturing device for driving the image capturing device to move in a horizontal coordinate plane.

In the embodiment of the present invention, during the process of loading, firstly, the image capturing device is moved so that the central position of the groove or hole of the blood vessel stent and the central position of the image capturing device are in the same longitudinal axis. Secondly, the blood vessel stent is moved so that the central position of the groove or hole of the blood vessel stent and the outlet of the loading device are in the same longitudinal axis. Finally, the outlet of the loading device is opened to perform the loading. During the aforesaid process of loading, not only the blood vessel stent but also the image capturing device are moved, and the loading device remains static.

Embodiment 3 of the Device

In the embodiment of the present invention, the device further comprises:

a position calibration device for calibrating a spatial position relation between a central position of the image capturing device and an outlet of the loading device; and a third position adjustment device connected with the memory unit and with the loading device for driving the loading device to move in a horizontal coordinate plane.

In the embodiments of the present application, the images of the grooves or holes of the medical appliance containing a plurality of grooves or holes are captured for multiple times, the image of each of the grooves or holes is processed, and then each of the grooves or holes is loaded concentratively, reducing the displacement movement route during the process of loading, shortening the loading time, and improving the loading speed and efficiency.

Besides, the embodiments of the present application search a groove core or a hole core using a machine visual theory, precisely locate each of the grooves or holes of the medical appliance, provide a precise coordinate for loading a medicament and/or polymer, and ensure the loading accuracy while loading rapidly.

Furthermore, the embodiments of the present application employ the intermittent loading manner, reduce the time waiting for evaporation of the medicament and/or polymer, not only shorten the loading time, but also make the loaded medicament and/or polymer more even, and improve the quality of loading the medicament and/or polymer.

For convenience of description, the aforesaid devices are divided into various units as per functions to be depicted respectively during the depiction. Surely, while the present application is carried out, it is feasible to realize the functions of every unit in the same one or multiple software and/or hardware.

As can be seen from the depictions of the aforesaid embodiments, those skilled in the art may clearly understand that the present application can be realized by means of software plus necessary universal hardware platform. Based on such understanding, the technical solution of the present application substantively or the portion that makes contribution to the existing technologies can be reflected in the form of a software product. The computer software product can be stored in a storage medium, such as a ROM/RAM, a disk, a Compact Disc and so on, and include a plurality of instructions for enabling a computer device (which may be a personal computer, a server, or a network device and so on) to execute the methods depicted in the embodiments of the present application or in some parts of the embodiments.

The above are only the specific means of carrying out the present invention. It shall be pointed out that under the premise of not deviating from the principle of the present application, an ordinary skilled person in the concerned technical field can make a plurality of improvements and modifications, which shall also be deemed to be the protection scope of the present application.

The invention claimed is:

1. A method for loading a medical appliance with a medicament and/or polymer, wherein the medical appliance contains a plurality of grooves or holes for being loaded with the medicament and/or polymer, characterized in comprising:

capturing images of the grooves or holes of the medical appliance for multiple times using an image capturing device, each image containing a pattern of at least one entire the groove or hole;

performing digital image processing on the image of each of the grooves or holes to obtain the pattern of each of the grooves or holes;

calculating a central position of the pattern of each of the grooves or holes based on the pattern of each of the grooves or holes, and determining a loading position of each of the grooves or holes based on the central position; and adjusting a relative position between a loading device and the medical appliance to align an outlet of the loading device with the loading position of each of the grooves or holes, and loading each of the grooves or holes with the medicament and/or polymer;

characterized in that the image processing is embodied as:

image converting that converts the image of each of the grooves or holes into a set of pixel points;

image pre-processing that performs a filter processing on the set of pixel points to remove image noise; and image processing that processes the pre-processed image with a binary method to obtain the pattern of each of the grooves or holes, and characterized in that the processing with a binary method is embodied as:

assigning a value to each of the pixel points with the binary method based on a gray value of each of the pre-processed pixel points, designating a pixel point conforming with a preset value or value range as a target pixel point or a background pixel point, and connecting all the pixel points designated as the target pixel points or the background pixel points to obtain the pattern of each of the grooves or holes.

2. The method according to claim 1, characterized in the calculating the central position of the pattern of each of the grooves or holes and determining the loading position of each of the grooves or holes based on the central position is embodied as:

calculating a spatial coordinate of a central pixel point of the pattern of each of the grooves or holes based on a spatial coordinate of each of the pixel points of the pattern of each of the grooves or holes;

determining a spatial coordinate of a geometrical center of the image of each of the grooves or holes;

calculating a coordinate difference value in the x direction and/or in the y direction between the spatial coordinate of the central pixel point of the pattern of each of the grooves or holes and the spatial coordinate of the geometrical center of the image of each of the grooves or holes, and recording it as a first relative position; and recording the first relative position corresponding to each of the grooves or holes as a first array.

3. The method according to claim 2, characterized in that the determining the spatial coordinate of the geometrical center of the image of each of the grooves or holes is embodied as:

obtaining spatial coordinates of four apexes of the image of each of the grooves or holes; and calculating the spatial coordinate of the geometrical center of the image of each of the grooves or holes based on the spatial coordinates of the four apexes.

4. The method according to claim 1, characterized in that the calculating the central position of the pattern of each of the grooves or holes, and determining the loading position of each of the grooves or holes based on the central position is embodied as:

calculating a pixel coordinate of the central pixel point of the pattern of each of the grooves or holes based on a pixel coordinate of each of the pixel points in the pattern of each of the grooves or holes;

determining a pixel coordinate of the pixel point of the geometrical center of the image of each of the grooves or holes;

calculating a coordinate difference value between the pixel coordinate of the central pixel point of the pattern of each of the grooves or holes and the pixel coordinate of the pixel point of the geometrical center of the image of each of the grooves or holes, converting the coordinate difference value between the two pixels points into a spatial coordinate difference value, and recording it as a first relative position; and recording the first relative position corresponding to each of the grooves or holes as a first array.

5. The method according to claim 4, characterized in that the determining the pixel coordinate of the pixel point of the geometrical center of the image of each of the grooves or holes is embodied as:

obtaining pixel coordinates of four apexes of the image of each of the grooves or holes; and calculating the pixel coordinate of the geometrical center of the image of each of the grooves or holes based on the pixel coordinates of the four apexes.

6. The method according to claim 5, characterized in that the calculating the pixel coordinate of the geometrical center of the image of each of the grooves or holes is embodied as:

obtaining a medium value of the pixel point respectively in an x direction and/or in a y direction based on a resolution of the image of each of the grooves or holes, the medium value being the pixel coordinate of the geometrical center of the image of each of the grooves or holes.

7. The method according to claim 2, characterized in the adjusting the relative position between the loading device and the medical appliance to align the outlet of the loading device with the loading position of the medical appliance is embodied as:

obtaining a spatial coordinate of the center of the image capturing device;

obtaining a spatial coordinate of the outlet of the loading device;

calculating a coordinate difference value in a x direction and/or in a y direction between the spatial coordinate of the center of the image capturing device and the spatial coordinate of the outlet of the loading device, and recording it as the second relative position;

moving the medical appliance in the x direction and/or in the y direction based on the first relative position and the second relative position to cause outlet of the loading device and the central position of the pattern of each of the grooves or holes to be in the same longitudinal axis; or moving the medical appliance in the x direction and/or in the y direction based on the first relative position to cause the central position of the pattern of each of the grooves or holes and the geometrical center of the image to be in the same longitudinal axis, and moving the loading device in the x direction and/or in the y direction based on the second relative position to cause the outlet of the loading device and the central position of the pattern of each of the grooves or holes to be in the same longitudinal axis.

8. The method according to claim 4, characterized in the adjusting the relative position between the loading device and the medical appliance to align the outlet of the loading device with the loading position of the medical appliance is embodied as:

obtaining a spatial coordinate of the center of the image capturing device;

obtaining a spatial coordinate of the outlet of the loading device;

calculating a coordinate difference value in a x direction and/or in a y direction between the spatial coordinate of the center of the image capturing device and the spatial coordinate of the outlet of the loading device, and recording it as the second relative position;

moving the medical appliance in the x direction and/or in the y direction based on the first relative position and the second relative position to cause outlet of the loading device and the central position of the pattern of each of the grooves or holes to be in the same longitudinal axis; or moving the medical appliance in the x direction and/or in the y direction based on the first relative position to cause the central position of the pattern of each of the grooves or holes and the geometrical center of the image to be in the same longitudinal axis, and moving the loading device in the x direction and/or in the y direction based on the second relative position to cause the outlet of the loading device and the central position of the pattern of each of the grooves or holes to be in the same longitudinal axis.

9. The method according to claim 2, characterized in that the adjusting the relative position between the loading device and the medical appliance to align the outlet of the loading device with the loading position of the medical appliance is embodied as:

moving the image capturing device in the x direction and/or in the y direction based on the first relative position in the first array to cause the central position of the pattern of each of the grooves or holes and the geometrical center of the image of each of the grooves or holes to be in the same longitudinal axis;

obtaining a spatial coordinate of a center of the image capturing device;

obtaining a spatial coordinate of the outlet of the loading device;

calculating a coordinate different value in the x direction and/or in the y direction between the spatial coordinate of the center of the image capturing device and the spatial coordinate of the outlet of the loading device, and recording it as the second relative position; and recording the second relative position corresponding to each of the grooves or holes as a second array;

moving the medical appliance or the loading device in the x direction and/or in the y direction based on the second relative position in the second array to cause the outlet of loading device and the central position of the pattern of each of the grooves or holes to be in the same longitudinal axis.

10. The method according to claim 4, characterized in that the adjusting the relative position between the loading device and the medical appliance to align the outlet of the loading device with the loading position of the medical appliance is embodied as:

moving the image capturing device in the x direction and/or in the y direction based on the first relative position in the first array to cause the central position of the pattern of each of the grooves or holes and the geometrical center of the image of each of the grooves or holes to be in the same longitudinal axis;

obtaining a spatial coordinate of a center of the image capturing device;

obtaining a spatial coordinate of the outlet of the loading device;

calculating a coordinate different value in the x direction and/or in the y direction between the spatial coordinate of the center of the image capturing device and the spatial coordinate of the outlet of the loading device, and recording it as the second relative position; and recording the second relative position corresponding to each of the grooves or holes as a second array;

moving the medical appliance or the loading device in the x direction and/or in the y direction based on the second relative position in the second array to cause the outlet of loading device and the central position of the pattern of each of the grooves or holes to be in the same longitudinal axis.

11. The method according to claim 1, characterized in that the loading each of the grooves or holes with the medicament or polymer is embodied as:

after causing the outlet of loading device and the central position of the pattern of each of the grooves or holes to be in the same longitudinal axis, opening the outlet of the loading device to load the grooves or holes with the medicament and/or polymer; and loading each of the grooves or holes with the medicament and/or polymer, wherein repeating the loading each of the grooves or holes with the medicament and/or polymer for multiple times based on a desired loading dose of the medicament and/or polymer.

12. The method according to claim 11, characterized in that the method further comprises: adjusting the position between the medical appliance and the image capturing device to cause other grooves or holes of the medical appliance to be located at an image capture position of the image capturing device.

* * * * *